US006569138B2

United States Patent
Helmfridsson et al.

(10) Patent No.: US 6,569,138 B2
(45) Date of Patent: *May 27, 2003

(54) SANITARY NAPKIN

(75) Inventors: Bror-Inge Helmfridsson, Partille (SE); Solgun Drevik, Molnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/832,976

(22) Filed: Apr. 12, 2001

(65) Prior Publication Data

US 2001/0031955 A1 Oct. 18, 2001

Related U.S. Application Data

(60) Provisional application No. 60/200,359, filed on Apr. 28, 2000.

(30) Foreign Application Priority Data

Apr. 13, 2000 (SE) ................................................ 0001378

(51) Int. Cl.[7] .................................................. A61F 13/15
(52) U.S. Cl. ................... 604/385.04; 604/387; 604/389
(58) Field of Search ....................... 604/385.01, 385.03, 604/385.05, 386, 387, 389

(56) References Cited

U.S. PATENT DOCUMENTS

| 5,453,143 A | | 9/1995 | Menard |
| 5,454,804 A | | 10/1995 | Widlund |
| 5,713,886 A | * | 2/1998 | Sturino .................. 604/385.04 |
| 5,729,835 A | * | 3/1998 | Williams ........................ 2/400 |

FOREIGN PATENT DOCUMENTS

WO    WO 00/30585    6/2000

* cited by examiner

Primary Examiner—Dennis Ruhl
Assistant Examiner—Jamisue A Webb
(74) Attorney, Agent, or Firm—Young & Thompson

(57) ABSTRACT

An absorbent article includes an absorbent body enclosed between a liquid-permeable outer sheet and a liquid-impermeable outer sheet, a front part facing forwards when the article is worn, and a rear part. The absorbent body tapers rearwardly to the end of the rear part from a section of greatest width situated in said front part. The article includes flexible outwardly projecting flaps which extend on respective sides of the absorbent body and have outer edges that are inclined relative to the longitudinal symmetry axis at an angle such that the distance between the outer sides of said flaps and the axis decreases in a direction towards the rear end of the article. At least two adhesive strings are applied to at least one of the flaps on the side thereof which, in the unfolded state of the flap, lies on the same side of the article as the liquid-impermeable outer sheet.

8 Claims, 1 Drawing Sheet

SANITARY NAPKIN

FIELD OF INVENTION

The present invention relates to an absorbent article, such as a sanitary napkin, a panty liner or an incontinence protector for women, that includes an absorption body sandwiched between a liquid-permeable and a liquid-impermeable outer sheet and having a front portion which is intended to face forwards when the article is worn, and a rear portion, wherein the absorbent body tapers rearwardly from a section of largest width situated in the front portion of the article to the rear portion thereof.

BACKGROUND OF THE INVENTION

A sanitary napkin of this nature is intended to be worn in so-called string panties, which are very narrow at the rear portion of the crotch part of the napkin. It is also desirable to provide sanitary napkins that are intended for string panties with outwardly projecting wings or flaps that are intended to be folded around the edges of a panty and fastened to the outside thereof and/or to each other, since such wings have been widely accepted in respect of sanitary napkins that are intended for use in conventional panties or underpants.

Flaps that are intended to be folded around the edges of string panties are narrow of necessity, and are folded around fold lines that are inclined to the longitudinal symmetry axis of the napkin. Sanitary napkins are normally produced in continuous process lines with the napkin blanks moving with their longitudinal axes coincidental with the machine direction. The glue strings applied to the liquid-impermeable outer sheet and to the outsides of the flaps are normally applied with the aid of glue nozzles or similar devices and therefore extend in the machine direction. Because the flaps of sanitary napkins intended for string panties are narrow and are inclined to the machine direction, it is not possible to apply glue strings of sufficient sizes on these flaps in the same manner as glue strings are applied to the flaps of sanitary napkins that are intended for use with conventional underpants or panties.

It is known in certain contexts to apply glue strings that are inclined to the machine direction, with the aid of a so-called label principle. The label principle involves the use of a rotating roll that includes an oblique pick-up surface which collects glue from a glue bath and applies the glue to a travelling web of material. Such a device is expensive. The use of the label principle also places a limitation on the types of glue that can be used in a sanitary napkin manufacturing line, because certain types of glue are liable to foam in the glue bath at the production rates prevailing in such manufacture. Production speeds of about 250 m/min are not unusual in the manufacture of sanitary napkins.

An object of the present invention is to solve the aforesaid problems associated with applying an adhesive to the flaps of a flap-equipped absorbent article in the form of a sanitary napkin, a panty liner or an incontinence protector for women intended for use in string panties.

SUMMARY OF THE INVENTION

This object is achieved with an absorbent article in the form of a sanitary napkin, a panty liner or an incontinence protector for women that includes an absorbent body which is sandwiched between a liquid-permeable and a liquid-impermeable outer sheet and that has a front part which is intended to face forwards in use, and a rear part, wherein the absorbent body tapers rearwardly from a section of greatest width situated in the front part of the article to the end of the rear part of said article, and wherein the article is characterised in that it includes outwardly projecting, flexible flaps which extend beyond respective sides of the absorbent body along a part of the tapering portion of said body and which have longitudinal edges that are inclined relative to the longitudinal symmetry axis of the article at an angle such that the distance between the outer sides of the flaps and the longitudinal symmetry axis of the article decreases towards the rear end of said article; and in that at least two strings of adhesive are applied to at least one of the flaps on that side of said flap which, in the unfolded state of the flap, lies on the same side of the article as said liquid-impermeable outer sheet, said strings extending parallel with the longitudinal symmetry axis of the article and being offset in relation to each another both longitudinally and transversely, wherein when the article is flat each rearwardly lying string is located closer to the longitudinal symmetry line of the article than the forwardly lying string. By utilising several short longitudinally extending adhesive strings that are offset relative to one another both longitudinally and transversely instead of a continuous inclined adhesive string, it is possible to provide an "inclined adhesive string" with the same type of equipment as that normally used in sanitary napkin manufacturing lines.

In one preferred embodiment of the invention, the flaps are integral parts of the outer sheets and at least one adhesive string is applied to that part of a napkin that includes the absorbent body. The adhesive used will preferably be a pressure-sensitive hotmelt glue. The adhesive strings applied to the flaps may also mutually overlap longitudinally. The adhesive strings applied to the flaps are preferably rectangular in shape and of mutually the same size, and an imaginary line that passes through the transversely innermost corners of the strings on one and the same flap will have the same angle of inclination to the longitudinal symmetry axis of the article as the outer longitudinal edge of said flap.

BRIEF DESCRIPTION OF THE DRAWING

The invention will now be described with reference to the accompanying drawing, in which.

DESCRIPTION OF EMBODIMENTS

Figure 1:
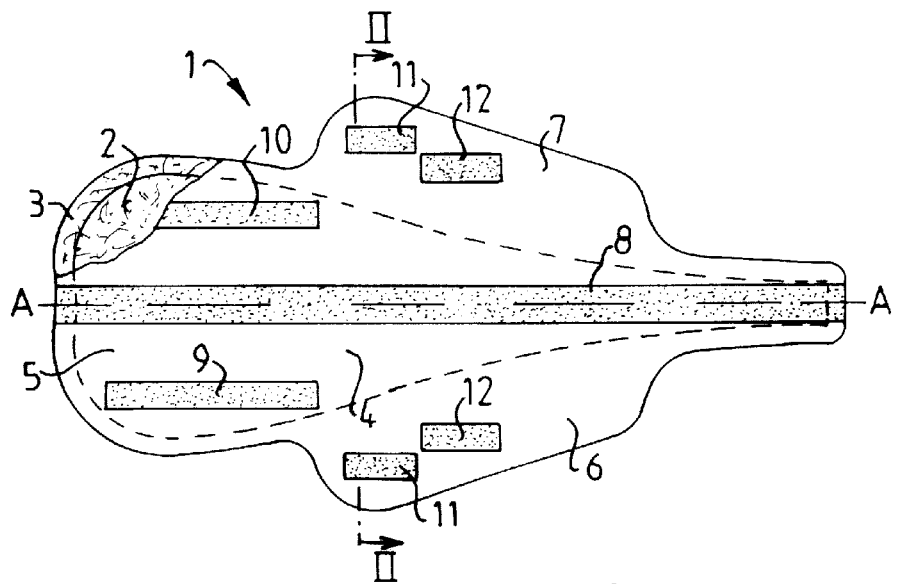
FIG. 1 is a schematic partially sectioned plan view of a first embodiment of an inventive sanitary napkin.

The sanitary napkin 1 shown in FIG. 1 typically includes an absorption body 2 that is enclosed between a liquid-permeable outer sheet 3 and a liquid-impermeable outer sheet or backing sheet 4. The outer sheets 3, 4 are mutually joined at parts which lie outside the absorbent body in some suitable way, e.g. by gluing or by ultrasound welding or heat welding.

The napkin 1 is intended for use in a string panty and the absorbent body 2 therefore tapers rearwardly from the widest part of a front portion 5 of the napkin to the rear end thereof. The outer sheets 3, 4 form outwardly projecting flaps 6, 7 or wings that are intended to be folded around the edges of a string panty and fastened to the outside thereof. The flaps 6, 7 extend longitudinally outside the edges of the absorbent body with essentially the same width, and the longitudinal edges of the flaps therewith converge towards each other in the rearward direction. In the illustrated embodiment, the length of the flaps corresponds to about half the length of the napkin and the flaps are spaced further from the front end of the napkin than from its rear end.

The illustrated napkin has a length of 140–260 mm. The absorbent body has a largest width of 70 mm and a smallest width of about 10 mm at its rear end. The flaps extend through a distance of about 25–30 mm beyond the edges of the absorbent body with the greatest distance at the forward portions of the flaps. The front edges of the flaps are located about 60 mm from the front edge of the napkin, and their rear edges are situated about 50 mm from the rear end of said napkin. It will be understood that these measurements are only intended to give a qualitative understanding of a suitable design of a sanitary napkin intended for string panties and in no way limit the scope of the invention.

The liquid-permeable outer sheet 3 is comprised of a soft skin-friendly material. This outer sheet may comprise different types of nonwoven fiber material. Other materials that can be used include perforated plastic films, plastic nets, knitted, crocheted or woven fabrics and combinations and laminations of said materials. The plastic may be a thermoplastic, e.g. polyethylene (PE). The nonwoven material may comprise natural fibers, such as cellulose or cotton, although it may alternatively comprise synthetic fibers, such as polyethylene (PE), polypropylene (PP), polyurethane (PU), a polyester, nylon or regenerated cellulose, or a mixture of different fibers. All materials used in the manufacture of liquid-permeable outer sheets for absorbent articles, such as sanitary napkins, panty liners or incontinence protectors can be used for the liquid-impermeable outer sheet 3 and it will be understood that the aforesaid material is given solely by way of example.

The liquid-impermeable outer sheet 4 is comprised of flexible material, preferably a thin plastic film of polyethylene (PE), polypropylene (PP) or a polyester, although it may consist of liquid-permeable material, such as nonwoven material, laminated with a liquid-impermeable material. All materials used to produce liquid-impermeable outer sheets for absorbent articles can be used. The outer sheet 4 may beneficially be air-permeable.

The absorbent body 2 is preferably composed from cellulose fibers, although other natural materials, such as cotton fibers or peat can be used. Alternatively, absorbent synthetic fibers or a mixture of natural fibers and synthetic fibers may be used. The absorbent body 2 may also include a superabsorbent, i.e. a polymer that is able to absorb liquid in an amount corresponding to several times its own weight. The absorbent body may also include shape stabilising means and liquid dispersing means, and also a binder which functions to hold short fibers and particles together in a coherent unit. The absorbent may also be comprised of more than one layer of absorbent material.

Although the flaps 6, 7 of the illustrated embodiment are comprised of laterally extended portions of the outer sheets 3, 4, they may comprise extended portions of solely one of said sheets. The flaps may also comprise separate pieces of material fastened to the sides of the napkin 1.

The liquid-impermeable outer sheet or backing sheet 4 of the napkin 1 is provided with three adhesive strings 8, 9, 10 in the region of the absorbent body 2, these being a central adhesive string 8 that extends along the longitudinal symmetry axis A—A of the napkin over the full length thereof, and two shorter adhesive strings 9, 10 that extend on respective sides of the central adhesive string 8 on the front part 5 of said napkin. These adhesive strings 8, 9, 10 are intended to fasten the napkin 1 to the inside of a string panty. Each of the adhesive strings 8, 9, 10 extend parallel with the longitudinal symmetry axis A—A of the napkin 1.

The napkin 1 is also provided with two adhesive strings 11, 12 on each flap 6, 7. These adhesive strings 11, 12 are relatively short and extend parallel with the longitudinal symmetry axis A—A of the napkin when the napkin is flat. The adhesive strings 11, 12 on each flap 6, 7 are also mutually spaced both longitudinally and laterally, wherewith the foremost string 11 is situated furthest from the longitudinal symmetry axis A—A. Each adhesive string 11, 12 will conveniently have a length shorter than about 30 mm, and preferably a length within the range of 10–20 mm. Each adhesive string will conveniently have a width of between 2–15 mm.

Although only two adhesive strings 11, 12 are disposed on each flap 6, 7 of the FIG. 1 embodiment, it will be understood that the flaps may be provided with more adhesive strings if so desired.

Figure 2:
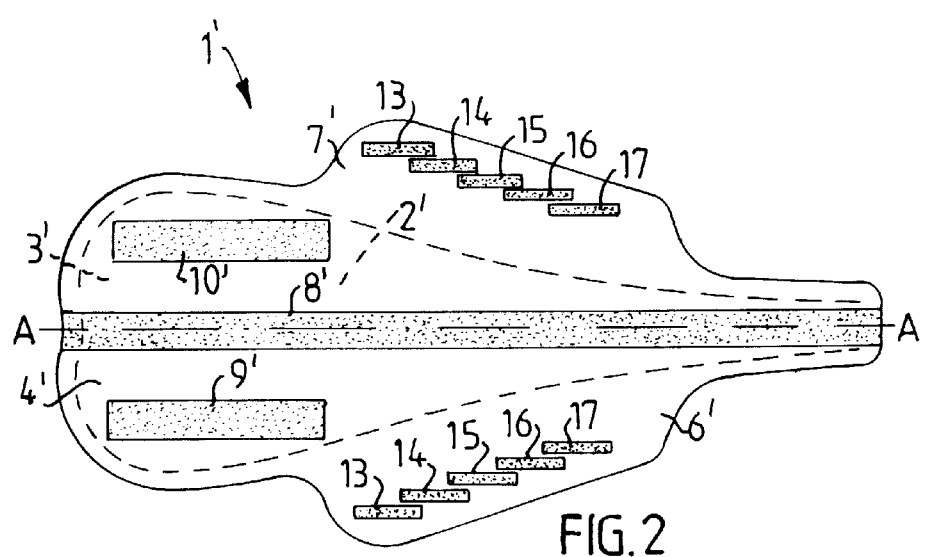
FIG. 2 is a schematic plan view of a second embodiment of an inventive sanitary napkin.

FIG. 2 illustrates a second embodiment of the invention that differs from the embodiment shown in FIG. 1 solely by the fact that the flaps 6', 7' are provided with an adhesive string pattern that is different to the pattern on the flaps 6, 7 of the FIG. 1 embodiment. Those components of the sanitary napkin 1' shown in FIG. 2 that find correspondence in similar components of the napkin 1 shown in FIG. 1 have been identified with the same reference sign to which a prime has been added. As opposed to the pattern of adhesive strings applied to the flaps 6, 7, which patterns do not extend over the rear portions of the flaps, the pattern of adhesive strings 13, 17 on the flaps 6', 7' extend longitudinally over the major part of said flaps. Furthermore, the adhesive strings 14–17 overlap forwardly lying adhesive strings in the longitudinal direction. Thus, the mutually overlapping short adhesive strings form an essentially continuous adhesive string that is inclined to the longitudinal symmetry axis A—A. The adhesive strings applied to the flaps are generally rectangular in shape and an imaginary line passing through the transversely innermost corners of the strings on one and the same flap is inclined to longitudinal symmetry axis of the article at the same angle as the outer longitudinal edge of said flap. The rectangular adhesive strings applied to the flaps will preferably have mutually the same size.

The adhesive in the adhesive strings is a pressure-sensitive hotmelt glue, e.g. Ecomelt H145 from Collano, Switzerland, although other commercially available pressure-sensitive adhesive can be used, including adhesives that are pressure-sensitive in a cold state, such as acrylate glue normally combined with stickiness-enhancing additives, such as polyterpene, or hotmelt glue such as styrene and butadiene co-polymers.

In the packaged state of the sanitary napkins 1, 1', the adhesive strings are covered by a protective layer, e.g. a layer of release paper that consists of silicone-coated paper and protects the adhesive strings against contaminants, such as dust and similar substances, and also prevents the glue from drying out prior to use. The napkin 1, 1' is conveniently provided with a central protective layer that is not removed until the time when the napkin shall be fastened to the inside of a string panty, and each flap is provided with a protective layer that is removed prior to folding the flap around the edge of a string panty and fastening said flap to the outside thereof. These protective layers or backings are not shown in the Figures for the sake of clarity.

The sanitary napkins 1, 1' are manufactured in so-called length production in a continuous production line, by which is meant that the machine direction coincides with the longitudinal axis of the napkin blanks. In production, absorbent bodies are placed on one travelling web of outer sheet material, whereafter the other web of outer sheet material is placed on the web that is comprised of the first outer sheet and the absorbent bodies. The adhesive strings and the protective layers may either be applied subsequent to having delivered outer sheeting and absorbent bodies to the production line, or may be applied to the liquid-impermeable outer sheet prior to combining said sheet with the absorbent bodies and the liquid-permeable outer sheet. Individual napkins are cut from the resultant web of napkin blanks in the final stage of manufacture.

The adhesive strings can either be applied to the protective layers prior to applying said layers to the liquid-impermeable outer sheet, or may be applied to the liquid-impermeable outer sheet prior to applying the protective layers.

The sanitary napkins 1, 1' or the liquid-impermeable outer sheet will thus have the flat state shown in the Figures when applying the adhesive strings.

Because the adhesive strings applied to the liquid-impermeable outer sheet all have a linear extension in the machine direction of the production line, the strings can be applied with the aid of simple glue nozzles or similar devices. Furthermore, the aforedescribed principle of creating generally continuous adhesive strings that extend in a direction which is inclined to the machine direction, by compiling the "continuous" adhesive strings from a number of short adhesive strings that are offset relative to each other both longitudinally and transversely, enables sanitary napkins that are provided with flaps and intended for wear in string panties to be provided with one or more continuous adhesive strings that are inclined relative to the machine direction on each flap without needing to use complicated glue applicating equipment and without the glue applying process detracting from the rate of production or the choice of adhesive.

It will be understood that the described embodiments can be modified within the scope of the invention. For instance, the absorbent body may include a central outwardly projecting part and the sanitary napkin may have dimensions other than those aforedescribed. The glue pattern on the part of the napkin that includes the absorbent body may also be different to that described, for instance the central adhesive string need not extend in the napkin over the whole of the front portion thereof, and the three adhesive strings disposed in the front portion of the napkin may be replaced with a single glue string that extends over the major part of the front portion of the napkin. More than three glue strings may be provided on the part of the napkin that includes the absorbent body. It is also conceivable to replace the adhesive strings in the region of the absorbent body with friction coatings or similar means. Moreover, adhesive strings may be provided solely on one flap, in which case it is necessary to dimension the flaps so that they overlap each other when folded in towards the underside of the string panty subsequent to having been folded around the edges thereof. The invention is therefore restricted solely by the contents of the accompanying Claims.

What is claimed is:

1. An absorbent article selected from the group consisting of a sanitary napkin, a panty liner and an incontinence protector for women, comprising an absorbent body that is enclosed between a liquid-permeable outer sheet and a liquid-impermeable outer sheet; said article having a front part which is intended to face forwards when the article is worn, and a rear part; said absorbent body continuously tapering rearwardly from a section of greatest width situated in the front part to an end of the rear part; said article including flexible outwardly projecting flaps which extend on respective sides of the absorbent body and have outer longitudinally extending edges that are inclined relative to a longitudinal symmetry axis of the article at an angle such that the distance between outer sides of said flaps and the longitudinal symmetry axis decreases in a direction towards a rear end of the article; at least one of the flaps having at least two adhesive strings comprising a forwardly lying string and a rearwardly lying string, on a side thereof which, in an unfolded state of the flap, lies on the same side of the article as the liquid-impermeable outer sheet; said adhesive strings extending parallel to the longitudinal symmetry axis and being offset relative to each other both longitudinally and transversely, whereby when the article is flat said rearwardly lying string is situated closer to the longitudinal symmetry axis than the forwardly lying string.

2. The absorbent article according to claim 1, wherein the flaps are integral with the outer sheets.

3. The absorbent article according to claim 1, further comprising at least one string of adhesive situated on the liquid impermeable outer sheet.

4. The absorbent article according to claim 1, wherein the adhesive strings on the consist of pressure-sensitive glue.

5. The absorbent article according to claim 4, wherein the adhesive strings comprise hotmelt glue.

6. The absorbent article according to claim 1, wherein the adhesive strings on the overlap each other in a longitudinal direction.

7. The absorbent article according to claim 6, wherein the adhesive strings on the are rectangular in shape; and an imaginary line passing through transversely innermost corners of the adhesive strings on one of the flaps is inclined to the longitudinal symmetry axis of the article at a same angle as the outer longitudinal edge of said one of the flaps.

8. The absorbent article according to claim 7, wherein the rectangular adhesive strings on the are mutually of the same size.

* * * * *